(12) United States Patent
Dworak et al.

(10) Patent No.: US 12,428,518 B2
(45) Date of Patent: Sep. 30, 2025

(54) (METH)ACRYLATE-FUNCTIONALIZED EXTENDED ISOSORBIDE

(71) Applicant: Henkel AG & Co. KGaA, Duesseldorf (DE)

(72) Inventors: David P. Dworak, Middletown, CT (US); Darel Gustafson, Shelton, CT (US); David Mullen, Navan (IE); Andrew D. Messana, Newington, CT (US); Aimee Hynes, Dublin (IE); Deirdre Ledwith, Dublin (IE); Ruairi O'Kane, Dublin (IE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/723,583

(22) Filed: Oct. 3, 2017

(65) Prior Publication Data
US 2018/0022848 A1    Jan. 25, 2018

Related U.S. Application Data

(63) Continuation of application No. PCT/US2016/017332, filed on Feb. 10, 2016.

(60) Provisional application No. 62/142,613, filed on Apr. 3, 2015.

(51) Int. Cl.
| | |
|---|---|
| *C08G 18/32* | (2006.01) |
| *C07D 493/04* | (2006.01) |
| *C08F 220/34* | (2006.01) |
| *C08F 222/10* | (2006.01) |
| *C08F 299/06* | (2006.01) |
| *C08G 18/04* | (2006.01) |
| *C08G 18/62* | (2006.01) |
| *C08G 18/67* | (2006.01) |
| *C08G 18/75* | (2006.01) |
| *C08G 18/80* | (2006.01) |
| *C08G 18/81* | (2006.01) |
| *C08G 81/02* | (2006.01) |
| *C08L 35/02* | (2006.01) |
| *C09D 175/16* | (2006.01) |
| *C09J 175/16* | (2006.01) |

(52) U.S. Cl.
CPC ....... *C08G 18/3218* (2013.01); *C07D 493/04* (2013.01); *C08F 222/10* (2013.01); *C08F 299/065* (2013.01); *C08G 18/04* (2013.01); *C08G 18/6225* (2013.01); *C08G 18/672* (2013.01); *C08G 18/755* (2013.01); *C08G 18/8016* (2013.01); *C08G 18/8116* (2013.01); *C08G 81/024* (2013.01); *C08L 35/02* (2013.01); *C09D 175/16* (2013.01); *C09J 175/16* (2013.01); *C08F 220/343* (2020.02); *C08F 222/102* (2020.02); *C08G 2190/00* (2013.01)

(58) Field of Classification Search
CPC .. C08F 220/34; C08F 299/065; C08F 222/10; C08F 2220/343; C08F 2222/1013; C08F 220/343; C08F 222/102; C08G 18/04; C08G 18/8116; C08G 18/8016; C08G 18/755; C08G 18/672; C08G 81/024; C08G 18/6225; C08G 2190/00; C08G 18/3218; C08L 35/02; C09J 175/16; C09D 175/16; C07D 493/04
See application file for complete search history.

(56) References Cited

U.S. PATENT DOCUMENTS

| | | | |
|---|---|---|---|
| 3,425,988 A * | 2/1969 | Toback | C09J 175/16 560/25 |
| 4,451,627 A * | 5/1984 | Frisch, Jr. | C09J 175/16 528/69 |
| 6,232,431 B1 * | 5/2001 | Hosoki | C08F 283/006 528/196 |
| 6,891,053 B2 | 5/2005 | Chasar et al. | |
| 7,619,046 B2 | 11/2009 | Broughton et al. | |
| 7,790,354 B2 * | 9/2010 | Ishigaki | G03F 7/027 430/270.1 |
| 8,575,378 B2 | 11/2013 | Garrett et al. | |
| 10,227,507 B2 | 3/2019 | O'Kane et al. | |
| 2009/0298970 A1 * | 12/2009 | Attarwala | C08F 265/06 523/201 |
| 2010/0006208 A1 * | 1/2010 | Attarwala | C08G 18/10 156/91 |
| 2014/0200288 A1 | 7/2014 | Xiaoming et al. | |
| 2015/0232610 A1 | 8/2015 | Leitner | |
| 2015/0299368 A1 | 10/2015 | Leitner et al. | |
| 2016/0068708 A1 | 3/2016 | Tanabiki | |

FOREIGN PATENT DOCUMENTS

| | | | |
|---|---|---|---|
| JP | 2011145330 | 7/2011 | |
| WO | WO-8202048 A * | 6/1982 | ........... C08F 220/36 |
| WO | 2013144033 | 10/2013 | |
| WO | WO 2014/064072 A1 * | 5/2014 | |
| WO | WO 2014/064097 A1 * | 5/2014 | |
| WO | 2014174861 | 10/2014 | |

OTHER PUBLICATIONS

International Search Report issued in connection with International Patent Application No. PCT/US2016/017332 mailed May 26, 2016.

* cited by examiner

*Primary Examiner* — Rabon A Sergent
(74) *Attorney, Agent, or Firm* — Steven C. Bauman

(57) ABSTRACT

The present invention relates to curable polyurethane polymers made from renewable materials. In particular isosorbide derived from glucose is used. These renewable materials may be formed into curable polyurethane polymer compositions having different chemical functionalities and cure mechanisms.

12 Claims, 2 Drawing Sheets

Break torque comparison on Black Oxide nuts & bolts

Break torque comparison on Zinc Phosphate nuts & bolts

Break torque comparison on Stainless Steel nuts & bolts

Hot Strength comparison at 150 and 180°C – 5N·m pre-torqued Zinc Phosphate nuts & bolts

(METH)ACRYLATE-FUNCTIONALIZED EXTENDED ISOSORBIDE

BACKGROUND

Field

The invention relates generally to (meth)acrylate-functionalized extended isosorbide, compositions made therefrom and methods to make curable compositions therewith.

Brief Description of Related Technology

There is a current emphasis on renewable sources for materials, particularly as a means of replacing petroleum-based products. A number of companies have focused on modifying plant oils to include functional groups which are useful for further reactions and producing polymer materials. For example, U.S. Pat. No. 6,891,053 discloses a method of making oleochemical oil-based polyols by mixing an epoxidized oleochemical, such as a vegetable or animal fat, and an alcohol using an activated or acid leached-clay to form the oleo-chemical oil-based polyol. U.S. Pat. Nos. 8,757,294 and 8,575,378 disclose other methods of making modified plant-based polyols by using a plant oil which includes at least one C=C group and reacting that group with a nucleophilic functional group and an active hydrogen group. The result is specific plant oils which have hydroxyl functionalization useful for further reaction, such as the reaction with an amine compound to form a polyurethane.

Recently, some modified plant oils having hydroxyl functionality have become available as renewable sources for starting materials in synthetic schemes. For example, several soy-based polyols sold under the brand Agrol by Biobased Technologies, Springdale, Arkansas, are disclosed as being useful sources of renewable polyols which may be used for making polyurethanes.

There is need for a process which uses renewable materials such as plant oils to form polyurethane polymers which contain (meth)acrylate, alkoxy, and other functionality. There is also a need for reactive fillers which can be made from renewable materials and incorporated into useful compositions for applications such as adhesives, sealants and coatings.

SUMMARY

In one aspect of the invention there is provided a (meth)acrylate functionalized isosorbide corresponding to the structure:

MA-U-A-U-MA wherein A includes an isosorbide unit, U includes a urethane linkage and MA includes a member selected from the group consisting of a (meth)acrylate-containing group, an acrylate-containing group and combinations thereof. For purposes of the present invention the term "(meth)acrylate" includes methacrylates and acrylates.

In another aspect of the invention there is provided a polymerizable resin which includes:
a) polymer corresponding to the structure:

MA-U-A-U-MA wherein A includes isosobide unit, U includes a urethane linkage and MA includes s a (meth)acrylate-containing group;

b) a cure system which includes a free radical initiator system.

In yet another aspect of the invention there is provided a method for forming a polymerizable (meth)acrylate-functionalized polyurethane polymer including, reacting a (meth)acrylate-functionalized isocyanate compound with an isosorbide unit, said reacting being conducted for a time and at a temperature sufficient to form a polymerizable (meth)acrylate-functionalized polyurethane compound.

DETAILED DESCRIPTION

Figure 1:
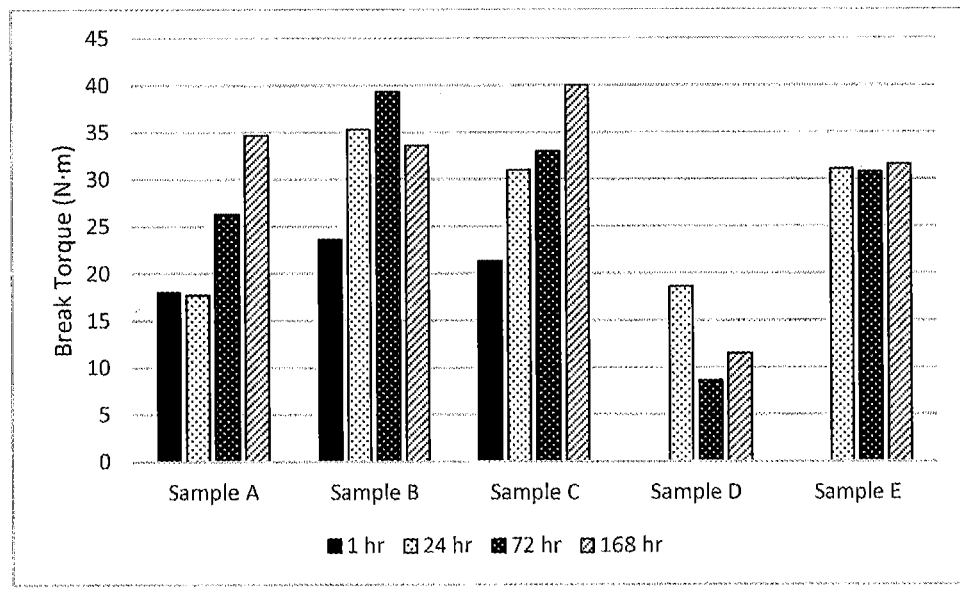
FIG. 1 shows a bar graph of the breakaway torque strengths of compositions of the invention at various room temperature cure times on black/oxide/mild steel nuts and bolts.
Figure 2:
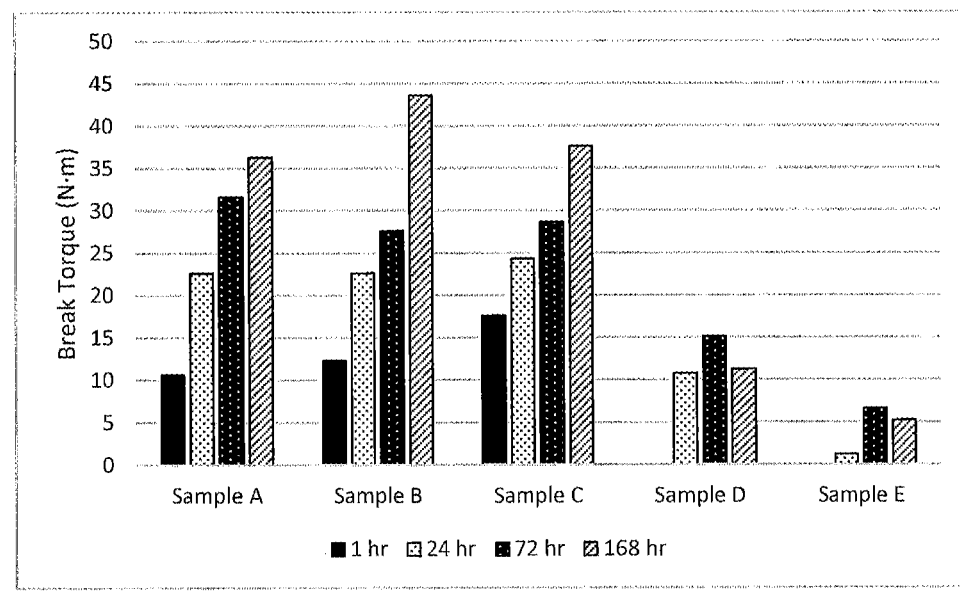
FIG. 2 shows a bar graph of the breakaway torque strengths of compositions of the invention at various room temperature cure times on zinc phosphate nuts and bolts.
Figure 3:
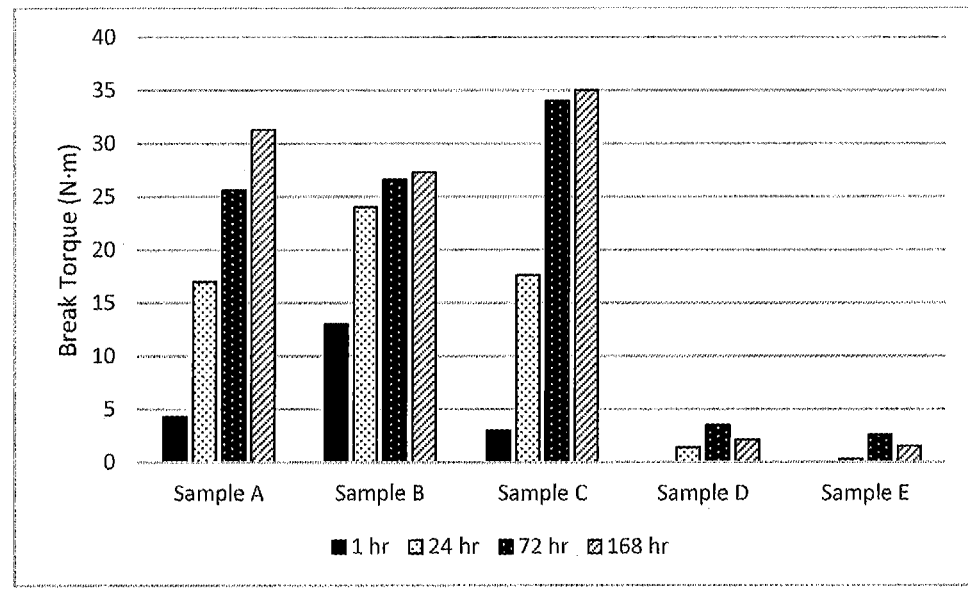
FIG. 3 shows a bar graph of the breakaway torque strengths of compositions of the invention at various room temperature cure times on stainless steel nuts and bolts.

The present invention uses the renewable material, isosorbide, to produce (meth)acrylate functionalized compounds and compositions made therefrom. This invention provides additives, such as reactive fillers, made from extended isosorbide units which can provide comparable or better properties than traditional fillers made from non-renewable materials.

Isosorbide is a non-toxic diol produced from biobased feedstocks. It is a heterocyclic compound that is derived from glucose. Isosorbide and its two isomers, namely isoidide and isomannide, are 1,4:3,6-dianhydrohexitols. It is a white solid that is prepared from the double dehydration of sorbitol. Isosorbide is biodegradable and thermally stable.

The present invention includes the use of such bio-based polyols, for either direct reaction with an appropriate (meth)acrylate-containing compound to form curable polyurethanes, or via an extended method, which includes first reacting the bio-based polyol with a diisocyanate and then further reacting the resultant product with a hydroxyl-containing (meth)acrylate, to yield a (meth)acrylated polyurethane. Moreover, additional modifications of the bio-based polyol may be made such that NCO groups may be incorporated into the bio-based polyol.

Isosorbide has the structure:

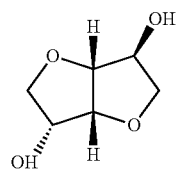

The present invention provides functionalized, and desirably multi-functionalized compounds useful in a variety of applications, including as sealants, adhesives and coatings, as well as being used as building blocks for polymers.

One aspect of the invention includes the reaction of isosorbide with a compound having methacrylate and isocyanato functionalization to yield the following reaction:

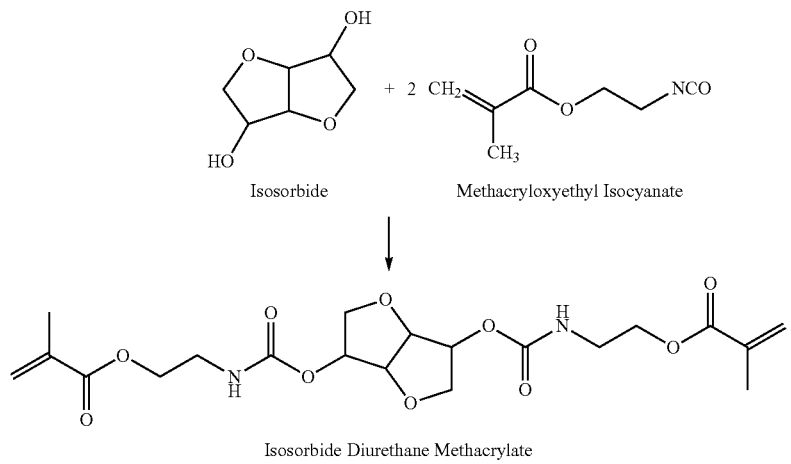

Diisocyantes useful in the present invention include, without limitation, isophorone diisocyanate (IPDI), IPDI isocyanaurate, polymeric IPDI, naphthalene 1,5-diisocyanate (NDI), methylene bis-cyclohexylisocyanate, methylene diphenyl diisocyanate (MDI), polymeric MDI, toluene diisocyanate (TDI), isocyanaurate of TDI, TDI-trimethylolpropane adduct, polymeric TDI, hexamethylene diisocyanate (HDI), HDI isocyanaurate, HDI biurate, polymeric HDI, xylylene diisocyanate, hydrogenated xylylene diisocyanate, tetramethyl xylylene diisocyanate, p-phenylene diisocyanate, 3,3'-dimethyldiphenyl-4,4'-diisocyanate (DDDI), 2,2,4-trimethylhexamethylene diisocyanate (TMDI), norbornane diisocyanate (NDI), and 4,4'-dibenzyl diisocyanate (DBDI). Combinations of diisocyantes may also be used. Monoisocyantes may also be used in the present invention.

Among the useful (meth)acrylate-containing hydroxyl compounds useful for reaction with the NCO functionalized bio-based polyols include, without limitation, 2-hydroxyethyl methacrylate, 2-hydroxyethyl acrylate, 3-hydroxypropyl methacrylate, 3-hydroxypropyl acrylate, 2-hydroxypropyl acrylate, 4-hydroxybutyl acrylate, 3-hydroxybutyl acrylate, 2-hydroxybutyl acrylate, 3-(acryloyloxy)-2-hydroxypropyl methacrylate, 2-isocyanatoethyl methacrylate, 2-isocyanatoethyl acrylate, and poly(propylene glycol) (meth)acrylate.

Among the useful (meth)acrylate-containing isocyanates useful for reaction with the bio-based polyols include, without limitation, 2-isocyanatoethyl acrylate, 2-isocyanatoethyl methacrylate, 3-isocyanatopropyl (meth)acrylate, 2-isocyanatopropyl (meth)acrylate, 4-isocyanatobutyl (meth)acrylate, 3-isocyanatobutyl (meth)acrylate, and 2-isocyanatobutyl (meth)acrylate.

As mentioned herein, when the bio-based polyol also includes other reactive groups such a NCO groups, resultant polyurethanes formed therefrom may have these groups available for further reactions. Thus, the inventive polyurethanes formed from the bio-based polyols used in the present invention allow for a variety of polyurethane end products having such functionalities as (meth)acrylate functionality, which in turn allows for free radical mechanisms to be employed in the final curable compositions made therefrom.

A variety of curable compositions may be made from the polyurethanes of the invention. For example, adhesive compositions, sealants and coatings are among the useful products which may be formed from the inventive renewable compositions. As previously mentioned, the compounds of the present invention may also be used as building blocks to make a variety of polymers.

The compositions made using the isosorbide-based compounds of the present invention may be incorporated into curable compositions having free radical and/or photocure mechanisms.

When incorporated into compositions which cure via free radical mechanisms, the compositions will usually include a free radical initiator. Examples of useful free radical initiators include, without limitation, hydroperoxides, such as cumene hydroperoxide, paramenthane hydroperoxide, tertiary butyl hydroperoxide, and peresters which hydrolyze to peroxides such as tertiary butyl perbenzoate, and the like. The amount of such peroxy compounds may vary from about 0.1 to about 10, preferably about 1 to about 5, percent by weight of the total composition.

When incorporated into compositions which photocure, the compositions will usually include a photoinitiator. Useful photoinitiators include, without limitation, 1-hydroxycyclohexyl phenyl ketone, 2-methyl-1-[4-(methylthio)phenyl]-2-morpholino propan-1-one, 2-benzyl-2-N,N-dimethylamino-1-(4-morpholinophenyl)-1-butanone, the combination of 1-hydroxy cyclohexyl phenyl ketone and benzophenone, 2,2-dimethoxy-2-phenyl acetophenone, the combination of bis(2,6-dimethoxybenzoyl-2,4,4-trimethyl pentyl) phosphine oxide and 2-hydroxy-2-methyl-1-phenyl-propan-1-one, and [bis(2,4,6-trimethyl benzoyl) phenyl phosphine oxide], 2-hydroxy-2-methyl-1-phenyl-1-propan-1-one, the combination of 2,4,6-trimethylbenzoyldiphenylphosphine oxide and 2-hydroxy-2-methyl-1-phenyl-propan-1-one, dl-camphorquinone, alkyl pyruvates, 2,2-dimethoxy-2-phenyl acetophenone, 2-hydroxy-2-methyl-1-phenyl-1-propane, bis(2,4,6-trimethyl benzoyl) phenyl phosphine oxide, bis(2,6-dimethoxybenzoyl-2,4,4-trimethylpentyl) phosphine oxide, 2-hydroxy-2-methyl-1-phenyl-propan-1-one, bis($n^5$-2,4-cyclopentadien-1-yl)-bis[2,6-difluoro-3-(1H-pyrrol-1-yl)phenyl]titanium, diethoxyacetophenone and combinations thereof. Photoinitiators may be used in amount of about 0.001% to about 2.0% by weight of the total composition.

Accelerators may also be advantageously included. Such accelerators include a variety of secondary and tertiary organic amines as well as sulfimides (e.g., benzoic sulfimide) which are also known in the art. These may be used at a concentration range of about 0.1 to about 5, desirably about 1 to about 2, percent by weight of the total composition.

Other agents such as thickeners, plasticizers, etc., are also known in the art and may advantageously be incorporated where functionally desirable, provided only that they do not interfere with the functioning of the additive for its intended purpose.

Syntheses for Preparing Curable Functionalized Polyurethane Polymers

The curable functionalized polyurethane polymers of the present invention may be formed using more than one method. Desirably the polyurethane polymers have (meth) acrylate functionality, but other functionalities are contemplated and may be achieved.

In a first method ("Direct Method"), the isosorbide component is directly reacted with a (meth)acrylate component containing a free NCO group to directly form curable (meth)acrylate-functionalized polyurethane polymers.

Desirably the equivalents ratio of OH:NCO in the reactants is about 0.1 to 3.0. More desirably the equivalents ratio of OH:NCO in the reactants is about 0.4 to about 2.0, and even more desirably about 0.8 to about 1.0 equivalents of OH:NCO.

The reaction is run in reactor with or without a suitable solvent. When solvents are employed, polar solvents such as toluene, tetrahydrofuran (THF), ethyl acetate, xylenes, and the like may be employed. The reaction is generally run at temperatures of about 25° C. to about 100° C., preferably about 40° C. to about 80° C., and more preferably about 60° C. to about 75° C. Metal-based catalysts, such as dibutyltin dilaurate among others as further described herein, may be used in amounts of about 0.01% to about 5 wt %, preferably 0.5% to about 2 wt %, and more preferably about 0.1% to about 1.0 wt %, based on the weight of the total reaction mixture. Desirably, the reaction is carried out for as long as required to substantially fully react the isocyanate and hydroxyl groups. Reaction times may range from about 2 to about 24 hours, preferably about 3 to about 12 hours, and more preferably about 4 to about 8 hours.

In a second method ("Extended Method") an isosorbide component is reacted with a diisocyanate to form a polyurethane intermediate. The stoichiometry of the reactants is controlled such that the polyurethane intermediate contains unreacted pendent NCO groups, intended to be used for further reaction. That is, pendent NCO groups remain on the polyurethane intermediate for further reaction with, for example, a hydroxyl containing (meth)acrylate component. The amount of residual NCO may be about 5 to 90 wt %, to preferably 25 to 70 wt %, and more preferably 30 to 60%.

The equivalents ratio of OH to NCO in the starting reactants diisocyanate components is about desirably 0.1 to about 10.0, more desirably about 0.2 to 3.0, and even more desirably about 0.5 to about 2.0 equivalents of OH to NCO. The reaction is run in a reactor with or without a suitable solvent. When solvents are employed, polar solvents such as toluene, THF, ethyl acetate, xylenes, and the like may be employed. The reaction is generally run at temperatures of about 25° C. to about 100° C., desirably about 40° C. to about 80° C., and more desirably about 60° C. to about 75° C. Metal-based catalysts, such as dibutyltin dilaurate, may be used in amounts of about 0.01% to about 5%, desirably 0.5% to about 2%, and more desirably about 0.1% to about 1.0%, based on the weight of the total reaction mixture. The reaction is carried out for as long as required to substantially fully react the hydroxyl groups with NCO groups. The reaction times may vary from about 2 to about 24 hours, desirably 3 to 12 hours, and more desirably 4 to 8 hours. Due to the excess NCO groups present in the reaction, the formed intermediate polyurethane will contain pendent NCO groups which are available for reaction with additional components. One particularly desirable further reaction includes the reaction of the intermediate polyurethane with an hydroxyl-containing (meth)acrylate component (e.g. 2-hydroxyethyl (meth)acrylate (HEMA)), to yield curable (meth)acrylate-functionalized polyurethane polymers. Desirably the equivalents ratio of NCO:OH in the reaction of the intermediate polyurethane with the hydroxyl-containing (meth) acrylate component is about 1:0.01 to about 1:1.2. This reaction yields a curable (meth)acrylate-functionalized polyurethane polymer useful for a variety of applications as previously mentioned. The reaction of the intermediate polyurethane with the hydroxyl-containing (meth)acrylate component is carried out for as long as required to fully react the isocyanate and hydroxyl groups. Typically, the reaction time may range from about 2 to about 12 hours, preferably about 3 to about 12 hours, and more preferably 4 to 8 hours.

The amount of renewable content present in the intermediate and final polymers made in accordance with the present invention may range from about 30% to about 70% by weight, more desirably about 45% to about 60% by weight.

The present invention provides a curable composition comprising
   a (meth)acrylate functionalized isosorbide corresponding to the structure:

wherein A comprises an isosorbide unit, U comprises a urethane linkage and MA comprises a member selected from the group consisting of a (meth)acrylate-containing group, an acrylate-containing group and combinations thereof and
   a cure system
   wherein the cure system is selected from the group consisting of a free radical initiator system,
   an anaerobic cure system, a heat cure system and combinations thereof.

The present invention provides a curable composition comprising
   a (meth)acrylate functionalized isosorbide corresponding to the structure:

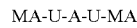

wherein A comprises an isosorbide unit, U comprises a urethane linkage and MA comprises a member selected from the group consisting of a (meth)acrylate-containing group, an acrylate-containing group and combinations thereof and
   a cure system
   wherein the cure system is selected from the group consisting of a free radical initiator system,
   an anaerobic cure system, a heat cure system and combinations thereof, the curable composition further comprising a (meth)acrylate component, wherein the (meth)acrylate component is selected from the group consisting of 2-hydroxyethyl methacrylate, 2-hydroxyethyl acrylate, 3-hydroxypropyl methacrylate, 3-hydroxypropyl acrylate, 2-hydroxypropyl acrylate, 4-hydroxybutyl acrylate, 3-hydroxybutyl acrylate, 2-hydroxybutyl acrylate, 3-(acryloyloxy)-2-hydroxypropyl methacrylate, 2-isocyanatoethyl methacrylate, 2-isocyanatoethyl acrylate, poly(propylene glycol) (meth)acrylate, 2-isocyanatoethyl acrylate, 2-isocyanatoethyl methacrylate, 3-isocyanatopropyl (meth)acrylate, 2-isocyanatopropyl (meth)acrylate, 4-isocyanatobutyl (meth)acrylate, 3-isocyanatobutyl (meth)acrylate, and 2-isocyanatobutyl (meth)acrylate.

EXAMPLES

As previously stated, isosorbide urethane compounds of the invention may be prepared in more than one method.

Example 1

In a first method, the reaction scheme is as follows:

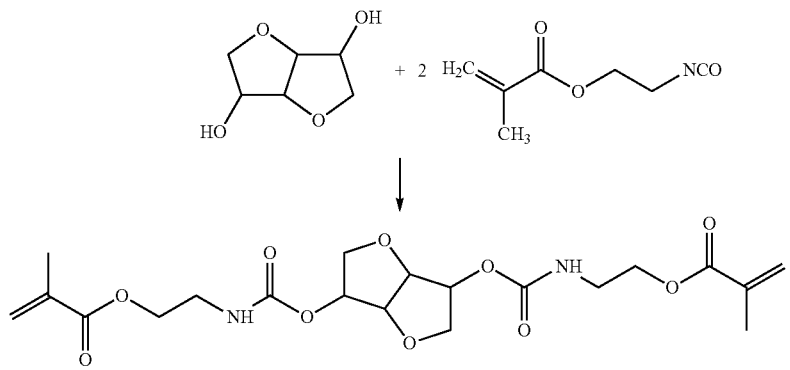

To the reaction vessel was added 25.00 grams (52.33)% of methacryloxyethyl isocyanate (MOI). To this was added dibutyltin dilaurate (DBTDL) in the amount of 0.19 grams (0.40%) and the vessel was heated to 75° C. To this mixture was added isosorbide in the amount of 22.55 grams (47.27%) and the reaction was allowed to run for about 4 hours, which was a sufficient amount of time to react all the NCO groups. Confirmation that all the NCO groups were consumed was performed using FT-IR which showed the absence of a peak at 2200 cm$^{-1}$.

Example 2

In a second method, the reaction scheme is as follows:

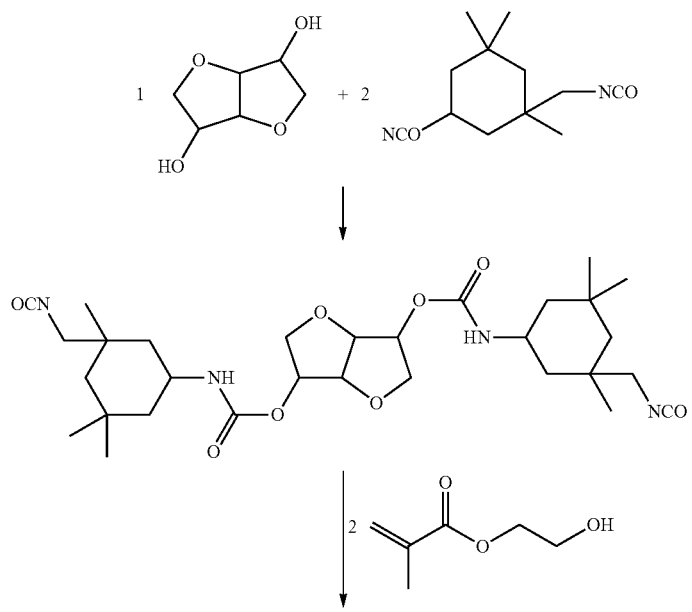

-continued

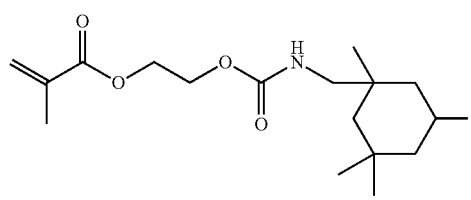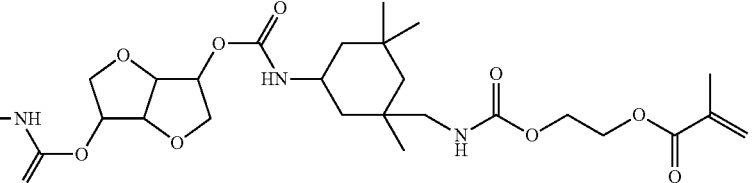

Isophorone diisocyanate (325.10 g, 1.4624 moles) and 200 mL of dry acetone are added to a 2-L jacketed polymerization reactor equipped with a thermocouple, stirrer, condenser, and nitrogen inlet/outlet. The contents were heated to a temperature of 65° C. Isosorbide (102.49 g, 0.731 moles) was then added and allowed to dissolve. Once dissolved dibutyltin dilaurate (0.29 g, 0.00046 moles) was then added and the temperature raised to 75° C. and the distilled acetone collected. The contents were allowed to react for +3 hours. A titration was then performed to determine the residual isocyanate content. Hydroxyethylmethacrylate (190.32 g, 1.462 moles, 1:1 residual NCO:OH equivalents) was then added and allowed to mix for +3 hours at 60° C. The methacrylated polyurethane was dropped (592.3 g, 95.8% yield) to yield a clear, colorless, and viscous resin.

Example 3

The isosorbide diurethane methacrylate synthesized in Example 1 above was used as a reactive filler in a model anaerobic adhesive formulation. Inventive Compositions A-E incorporate the reactive filler at various percentages and the resultant compositions were used as a threadlocker on various surfaces and tested. The test results are shown in FIGS. 1-4. The isosorbide diurethane methacrylate was evaluated. Samples A, B, C, D and E were prepared with approximate renewable carbon content of 48.4%, 47.4%, 46.4%, 45.4% and 44.4% respectively.

TABLE I

| Component | Sample (Wt %) | | | | |
| --- | --- | --- | --- | --- | --- |
| | A | B | C | D | E |
| (Meth)acrylate Component | 90.131 | 85.131 | 80.131 | 75.131 | 70.131 |
| Isosorbide Diurethane Methacrylate | 5 | 10 | 15 | 20 | 25 |
| Free radical Stabilizer | 0.385 | 0.385 | 0.385 | 0.385 | 0.385 |
| Metal Chelate Stabilizer | 0.215 | 0.215 | 0.215 | 0.215 | 0.215 |
| Sachharin | 0.913 | 0.913 | 0.913 | 0.913 | 0.913 |
| 1-Acetyl-2-phenylhydrazine | 0.173 | 0.173 | 0.173 | 0.173 | 0.173 |
| Maleic acid | 0.288 | 0.288 | 0.288 | 0.288 | 0.288 |
| Metal Chelate Stabilizer [1] | 0.65 | 0.65 | 0.65 | 0.65 | 0.65 |
| C.I. Solvent Green 3 | 0.02 | 0.02 | 0.02 | 0.02 | 0.02 |
| Solvent Yellow 16 | 0.013 | 0.013 | 0.013 | 0.013 | 0.013 |
| C.I. Solvent Yellow 14 | 0.001 | 0.001 | 0.001 | 0.001 | 0.001 |
| Fluorescent Agent | 0.769 | 0.769 | 0.769 | 0.769 | 0.769 |
| Cumene Hydroperoxide | 1.442 | 1.442 | 1.442 | 1.442 | 1.442 |
| Total | 100 | 100 | 100 | 100 | 100 |

Figure 4:
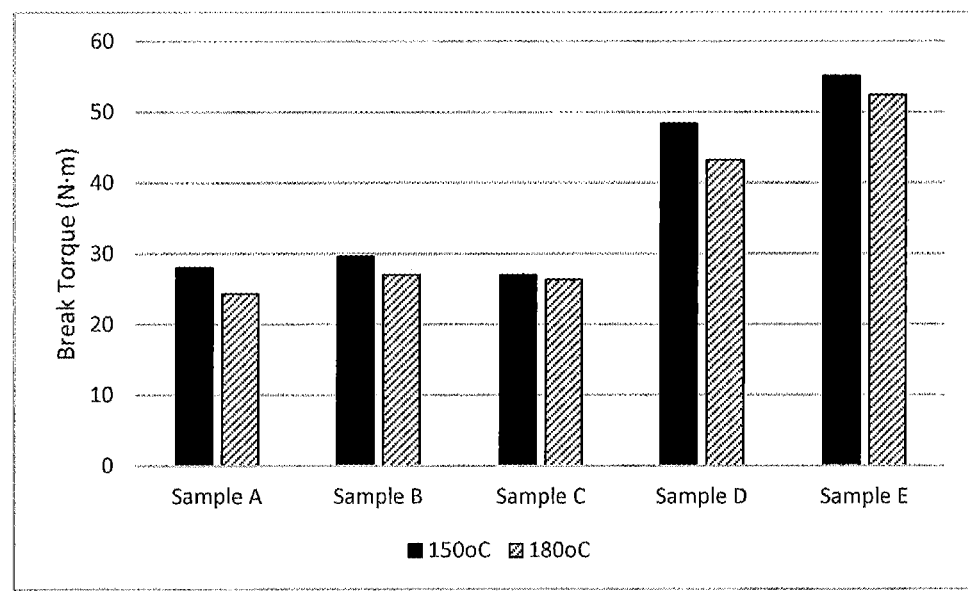
FIG. 4 shows a bar graph comparing the breakaway torque strengths of compositions of the invention on zinc phosphate (5N-m) pre-torqued nuts and bolts at elevated temperatures.

It is evident from the Figures that the introduction of isosorbide diurethane methacrylate as a reactive filler at loadings of 5% (A), 10% (B), 15% (C) 20% (D) and 25% (E) provides breakaway torque performances which are comparable to commercially available high performance threadlockers such as Loctite 270, on a variety of different surfaces and for different cure times at room temperature (FIGS. 1-3) as well as at high temperatures (FIG. 4).

The invention claimed is:
1. An anaerobically curable composition comprising
a (meth)acrylate component, an isosorbide diurethane (meth)acrylate, and
an anaerobic cure system;
wherein the isosorbide diurethane (meth)acrylate is the reaction product of an isosorbide and 2-isocyanatoethyl (meth)acrylate;
wherein the (meth)acrylate component is selected from the group consisting of 2-hydroxyethyl methacrylate, 2-hydroxyethyl acrylate, 3-hydroxypropyl methacrylate, 3-hydroxypropyl acrylate, 2-hydroxypropyl acrylate, 4-hydroxybutyl acrylate, 3-hydroxybutyl acrylate, 2-hydroxybutyl acrylate, 3-(acryloyloxy)-2-hydroxypropyl methacrylate, 2-isocyanatoethyl methacrylate, 2-isocyanatoethyl acrylate, poly(propylene glycol) (meth)acrylate, 2-isocyanatoethyl acrylate, 2-isocyanatoethyl methacrylate, 3-isocyanatopropyl (meth)acrylate, 2-isocyanatopropyl (meth)acrylate, 4-isocyanatobutyl (meth)acrylate, 3-isocyanatobutyl (meth)acrylate, and 2-isocyanatobutyl (meth)acrylate; and
wherein the (meth)acrylate component is present in an amount of 85 wt % and the isosorbide diurethane (meth)acrylate is present in an amount of 10 wt %, each based on the total weight of the composition, and wherein said composition after curing for 168 hours has a break torque of from 25 N·m to 30 N·m on black oxide nuts and bolts; or
wherein the (meth)acrylate component is present in an amount of 80 wt % and the isosorbide diurethane (meth)acrylate is present in an amount of 15 wt %, each based on the total weight of the composition, and wherein said composition after curing for 168 hours, has a break torque of from 30 N·m to 40 N·m on black oxide nuts and bolts; or
wherein the (meth)acrylate component is present in an amount of 75 wt % and the isosorbide diurethane (meth)acrylate is present in an amount of 20 wt %, each based on the total weight of the composition, and wherein said composition after curing has a break torque of from 30 N·m to 40 N·m on pre-torqued zinc phosphate nuts and bolts at a temperature of 150° C. or at a temperature of 180° C.; or
wherein the (meth)acrylate component is present in an amount of 70 wt % and the isosorbide diurethane (meth)acrylate is present in an amount of 25 wt %, each based on the total weight of the composition, and wherein said composition after curing has a break torque of from 40 N·m to 50 N·m on pre-torqued zinc phosphate nuts and bolts at a temperature of 150° C. or at a temperature of 180° C.
2. The composition of claim 1, wherein the composition further includes a metal-based catalyst.

3. The anaerobically curable composition of claim 1, wherein the (meth)acrylate component is present in an amount of 80 wt % and the isosorbide diurethane (meth) acrylate is present in an amount of 15 wt %, each based on the total weight of the composition, and wherein said composition after curing for 168 hours, has a break torque of from 30 N·m to 40 N·m on black oxide nuts and bolts.

4. The anaerobically curable composition of claim 1, wherein the (meth)acrylate component is present in an amount of 70 wt % and the isosorbide diurethane (meth) acrylate is present in an amount of 25 wt %, each based on the total weight of the composition, and wherein said composition after curing has a break torque of from 40 N·m to 50 N·m on pre-torqued zinc phosphate nuts and bolts at a temperature of 150° C. or at a temperature of 180° C.

5. The anaerobically curable composition of claim 1, wherein the (meth)acrylate component is present in an amount of 85 wt % and the isosorbide diurethane (meth) acrylate is present in an amount of 10 wt %, each based on the total weight of the composition, and wherein said composition after curing for 168 hours has a break torque of from 25 N·m to 30 N·m on black oxide nuts and bolts.

6. The anaerobically curable composition of claim 1, wherein the (meth)acrylate component is present in an amount of from 75 wt % and the isosorbide diurethane (meth)acrylate is present in an amount of 20 wt %, each based on the total weight of the composition, and wherein said composition after curing has a break torque of from 30 N·m to 40 N·m on pre-torqued zinc phosphate nuts and bolts at a temperature of 150° C. or at a temperature of 180° C.

7. An anaerobically curable composition comprising
a (meth)acrylate component, an isosorbide diurethane (meth)acrylate, and
an anaerobic cure system;
wherein the isosorbide diurethane (meth)acrylate is the reaction product of an isosorbide and an isocyanatoalkyl (meth)acrylate selected from the group consisting of 2-isocyanatoethyl (meth)acrylate, 3-isocyanatopropyl (meth)acrylate, 2-isocyanatopropyl (meth)acrylate, 4-isocyanatobutyl (meth)acrylate, 3-isocyanatobutyl (meth)acrylate, and 2-isocyanatobutyl (meth)acrylate;
wherein the (meth)acrylate component is selected from the group consisting of 2-hydroxyethyl methacrylate, 2-hydroxyethyl acrylate, 3-hydroxypropyl methacrylate, 3-hydroxypropyl acrylate, 2-hydroxypropyl acrylate, 4-hydroxybutyl acrylate, 3-hydroxybutyl acrylate, 2-hydroxybutyl acrylate, 3-(acryloyloxy)-2-hydroxypropyl methacrylate, 2-isocyanatoethyl methacrylate, 2-isocyanatoethyl acrylate, poly(propylene glycol) (meth)acrylate, 2-isocyanatoethyl acrylate, 2-isocyanatoethyl methacrylate, 3-isocyanatopropyl (meth)acrylate, 2-isocyanatopropyl (meth)acrylate, 4-isocyanatobutyl (meth)acrylate, 3-isocyanatobutyl (meth)acrylate, and 2-isocyanatobutyl (meth)acrylate; and
wherein the (meth)acrylate component is present in an amount of 85 wt % and the isosorbide diurethane (meth)acrylate is present in an amount of 10 wt %, each based on the total weight of the composition, and wherein said composition after curing for 168 hours has a break torque of from 25 N·m to 30 N·m on black oxide nuts and bolts; or
wherein the (meth)acrylate component is present in an amount of 80 wt % and the isosorbide diurethane (meth)acrylate is present in an amount of 15 wt %, each based on the total weight of the composition, and wherein said composition after curing for 168 hours, has a break torque of from 30 N·m to 40 N·m on black oxide nuts and bolts; or
wherein the (meth)acrylate component is present in an amount of 75 wt % and the isosorbide diurethane (meth)acrylate is present in an amount of 20 wt %, each based on the total weight of the composition, and wherein said composition after curing has a break torque of from 30 N·m to 40 N·m on pre-torqued zinc phosphate nuts and bolts at a temperature of 150° C. or at a temperature of 180° C.; or
wherein the (meth)acrylate component is present in an amount of 70 wt % and the isosorbide diurethane (meth)acrylate is present in an amount of 25 wt %, each based on the total weight of the composition, and wherein said composition after curing has a break torque of from 40 N·m to 50 N·m on pre-torqued zinc phosphate nuts and bolts at a temperature of 150° C. or at a temperature of 180° C.

8. The anaerobically curable composition of claim 7, wherein the (meth)acrylate component is present in an amount of 80 wt % and the isosorbide diurethane (meth) acrylate is present in an amount of 15 wt %, each based on the total weight of the composition, and wherein said composition after curing for 168 hours, has a break torque of from 30 N·m to 40 N·m on black oxide nuts and bolts.

9. The anaerobically curable composition of claim 7, wherein the (meth)acrylate component is present in an amount of 70 wt % and the isosorbide diurethane (meth) acrylate is present in an amount of 25 wt %, each based on the total weight of the composition, and wherein said composition after curing has a break torque of from 40 N·m to 50 N·m on pre-torqued zinc phosphate nuts and bolts at a temperature of 150° C. or at a temperature of 180° C.

10. The anaerobically curable composition of claim 7, wherein the (meth)acrylate component is present in an amount of 85 wt % and the isosorbide diurethane (meth) acrylate is present in an amount of 10 wt %, each based on the total weight of the composition, and wherein said composition after curing for 168 hours has a break torque of from 25 N·m to 30 N·m on black oxide nuts and bolts.

11. The anaerobically curable composition of claim 7, wherein the (meth)acrylate component is present in an amount of from 75 wt % and the isosorbide diurethane (meth)acrylate is present in an amount of 20 wt %, each based on the total weight of the composition, and wherein said composition after curing has a break torque of from 30 N·m to 40 N·m on pre-torqued zinc phosphate nuts and bolts at a temperature of 150° C. or at a temperature of 180° C.

12. An anaerobically curable composition comprising
a (meth)acrylate component, isosorbide diurethane methacrylate, and
an anaerobic cure system;
wherein the isosorbide diurethane methacrylate is the reaction product of an isosorbide and 2-isocyanatoethyl methacrylate;
wherein the (meth)acrylate component is selected from the group consisting of 2-hydroxyethyl methacrylate, 2-hydroxyethyl acrylate, 3-hydroxypropyl methacrylate, 3-hydroxypropyl acrylate, 2-hydroxypropyl acrylate, 4-hydroxybutyl acrylate, 3-hydroxybutyl acrylate, 2-hydroxybutyl acrylate, 3-(acryloyloxy)-2-hydroxypropyl methacrylate, 2-isocyanatoethyl methacrylate, 2-isocyanatoethyl acrylate, poly(propylene glycol) (meth)acrylate, 2-isocyanatoethyl acrylate, 2-isocyanatoethyl methacrylate, 3-isocyanatopropyl (meth)acrylate, 2-isocyanatopropyl (meth)acrylate, 4-isocyanatobutyl (meth)acrylate, 3-isocyanatobutyl (meth)acrylate, and 2-isocyanatobutyl (meth)acrylate;

wherein the (meth)acrylate component is present in an amount of 80 wt % and the isosorbide diurethane (meth)acrylate is present in an amount of 15 wt %, each based on the total weight of the composition, and wherein said composition after curing for 168 hours, has a break torque of from 30 N·m to 40 N·m on black oxide nuts and bolts; or wherein the (meth)acrylate component is present in an amount of 70 wt % and the isosorbide diurethane (meth)acrylate is present in an amount of 25 wt %, each based on the total weight of the composition, and wherein said composition after curing has a break torque of from 40 N·m to 50 N·m on pre-torqued zinc phosphate nuts and bolts at a temperature of 150° C. or at a temperature of 180° C.

* * * * *